US00PP14753P2

(12) United States Plant Patent
Trees

(10) Patent No.: US PP14,753 P2
(45) Date of Patent: May 4, 2004

(54) DAHLIA PLANT NAMED 'PATRICIA'

(50) Latin Name: *Dahlia variaibilis*
Varietal Denomination: Patricia

(75) Inventor: Scott C. Trees, Shell Beach, CA (US)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/624,103

(22) Filed: Jul. 21, 2003

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—Annette H Para
(74) *Attorney, Agent, or Firm*—C. A. Whealy

(57) ABSTRACT

A distinct cultivar of Dahlia plant named 'Patricia', characterized by its upright plant habit; freely branching habit; semi-double type inflorescences; and light orange and red bi-colored ray florets.

1 Drawing Sheet

Botanical classification/cultivar designation: *Dahlia variabilis* cultivar Patricia.

BACKGROUND OF THE INVENTION

The present Invention relates to a new and distinct cultivar of Dahlia plant, botanically known as *Dahlia variabilis,* commercially referred to as a pot-type Dahlia, and hereinafter referred to by the cultivar name 'Patricia'.

The new Dahlia is a naturally-occurring branch sport of the Dahlia cultivar Connie, disclosed in U.S. Plant Pat. No. 6,768. The new Dahlia was discovered by the Inventor in a controlled environment in Arroyo Grande, Calif. in April, 1997.

Asexual reproduction of the new Dahlia by stem cuttings was first conducted in Arroyo Grande, Calif. in 1997. Asexual reproduction by cuttings has shown that the unique features of this new Dahlia are stable and reproduced true to type in successive generations.

SUMMARY OF THE INVENTION

The cultivar Patricia has not been observed under all possible environmental conditions. The phenotype may vary somewhat with variations in environment such as temperature and daylength, without, however, any variance in genotype.

The following traits have been repeatedly observed and are determined to be the unique characteristics of 'Patricia'. These characteristics in combination distinguish 'Patricia' as a new and distinct pot-type Dahlia:

1. Upright plant habit.
2. Freely branching habit.
3. Semi-double type inflorescences.
4. Light orange and red bi-colored ray florets.

Plants of the new Dahlia differ from plants of the parent, the cultivar Connie, primarily in ray floret coloration as plants of the cultivar Connie have bright orange red-colored ray florets.

Plants of the new Dahlia can be compared to plants of the Dahlia cultivar Margaret, disclosed in U.S. Plant Pat. No. 6,769. In side-by-side comparisons conducted in West Chicago, Ill., plants of the new Dahlia had larger leaves and were more freely branching than plants of the cultivar Margaret. In addition, plants of the new Dahlia and the cultivar Margaret differed in ray floret color as plants of the cultivar Margaret had bright yellow-colored ray florets.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph at the top of the sheet comprises a side perspective view of a typical flowering plant of 'Patricia'.

The photograph at the bottom of the sheet is a close-up view of a typical inflorescence of 'Patricia'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown and flowered during the spring in West Chicago, Ill., under commercial practice in a polycarbonate-covered greenhouse. During the production the plants, day temperatures ranged from 18 to 24° C., night temperatures ranged from 16 to 18° C., and light levels ranged from 4,000 to 6,000 footcandles. One cutting was planted per 10-cm container and plants were grown for about 12 weeks.

Botanical classification: *Dahlia variabilis* cultivar Patricia.

Parentage: Naturally-occurring branch mutation of '*Dahlia variabilis*' cultivar Connie, disclosed in U.S. Plant Pat. No. 6,768.

Propagation:

*Type.*—By stem cuttings.

*Time to rooting.*—About 7 days at 18° C.

*Time to develop a rooted cutting.*—About 21 days at 18° C.

*Root description.*—Fibrous; development of tubers has not been observed.

Plant description:

*Appearance.*—Herbaceous pot-type Dahlia. Inverted triangle; upright and somewhat mounded plant habit. Freely branching, about six lateral branches per plant.

*Plant height.*—About 38 cm.

*Plant width or area of spread.*—About 26 cm.

*Lateral branches.*—Length: About 18 cm. Diameter: About 2.9 mm. Internode length: About 4.1 cm. Strength: Strong. Texture: Smooth, glabrous. Color: 144B overlain with 178A.

*Foliage description.*—Arrangement: Opposite; compound, usually three leaflets per leaf. Leaf length: About 9.8 cm. Leaf width: About 9.8 cm. Leaflet shape: Ovate. Leaflet apex: Acuminate. Leaflet base: Attenuate. Leaflet margin: Serrate. Texture, upper surface: Leathery; sparsely pubescent along midvein. Texture, lower surface: Leathery; smooth, glabrous. Venation pattern: Pinnate. Petiole length: About 4.1 cm. Petiole diameter: About 2.7 mm. Petiole texture, upper and lower surfaces: Smooth, glabrous. Color: Developing and fully expanded foliage, upper surface: 146A. Developing and fully expanded foliage, lower surface: Between 147B and 147C. Venation, upper and lower surfaces: 147C. Petiole, upper surface: 146C overlain with 59A. Petiole, lower surface: 146C.

Inflorescence description:

*Appearance.*—Terminal semi-double type inflorescences held above and beyond the foliage on strong flexible peduncles; inflorescences face mostly upright. Composite inflorescence form with ovate-shaped ray florets and disc florets massed at the center; ray and disc florets develop acropetally on a capitulum. Inflorescences not fragrant. Inflorescences persistent.

*Flowering response.*—Plants flower continuous and freely from spring until fall.

*Postproduction longevity.*—Inflorescences maintain good color and substance for about five to seven days on the plant.

*Quantity of inflorescences.*—One inflorescence per peduncle; about ten opened inflorescences and inflorescence buds per plant.

*Inflorescence bud* (*stage of showing color*).—Shape: Oblate. Length: About 1.6 cm. Diameter: About 1.8 cm. Color: 25C with random streaks of 45A.

*Inflorescence size.*—Diameter: About 8.5 cm. Depth (height): About 3.1 cm. Disc diameter: About 2.1 cm.

*Ray florets.*—Shape: Ovate. Aspect: Straight, concave. Length: About 3.3 cm. Width: About 1.8 cm. Apex: Acute to emarginate. Base: Fused into a short corolla tube. Margin: Entire. Texture, upper and lower surfaces: Smooth, glabrous. Number of ray florets per inflorescence: About 34 arranged in about four rows. Color: When opening and fully opened, upper surface: Ground color, 25C; random streaks and spots, 45B; towards the base, closer to 3A. When opening and fully opened, lower surface: Ground color, 26B; random streaks and spots, 42B.

*Disc florets.*—Shape: Tubular, elongated. Apex: Five-pointed. Length: About 8 mm. Width: About 2 mm. Number of disc florets per inflorescence: About 40. Color: 12A.

*Involucral bracts.*—Quantity: About eight. Length: About 2 cm. Width: About 5 mm. Shape: Lanceolate. Apex: Acute. Base: Truncate. Margin: Entire. Texture, upper and lower surfaces: Smooth, glabrous. Color, upper and lower surfaces: Towards the base, 143B; gradually fading closer to 145C towards the apex.

*Peduncles.*—Length: About 12.1 cm. Diameter: About 3 mm. Strength: Strong, flexible. Aspect: Erect. Texture: Smooth, glabrous. Color: 144A with random streaks of 59A.

*Reproductive organs.*—Androecium: Present on disc florets only. Quantity per floret: One. Anther length: About 2.6 mm. Anther color: 20A. Pollen amount: Moderate. Pollen color: 17A. Gynoecium: Present on both ray and disc florets. Quantity per floret: One. Pistil length: About 9 mm. Stigma length: About 4 mm. Stigma color: 14A. Style color: 150C. Ovary color: 145A.

*Seed/fruit.*—Seed and fruit production has not been observed.

Disease/pest tolerance: Plants of the new Dahlia have not been observed to be tolerant to pathogens and pests common to Dahlias.

It is claimed:

1. A new and distinct cultivar of Dahlia plant named 'Patricia', as illustrated and described.

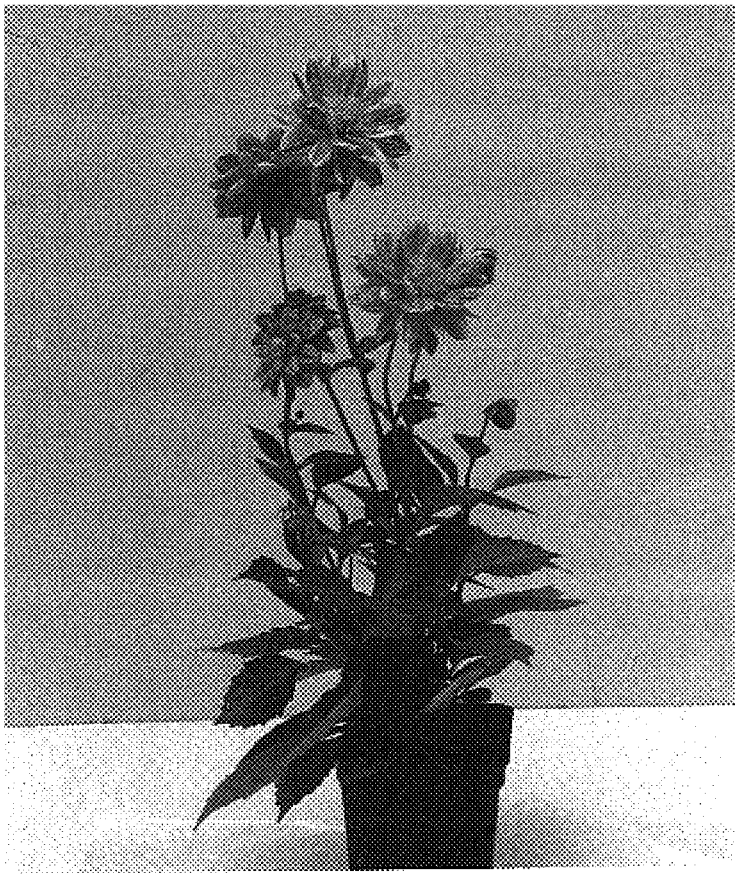
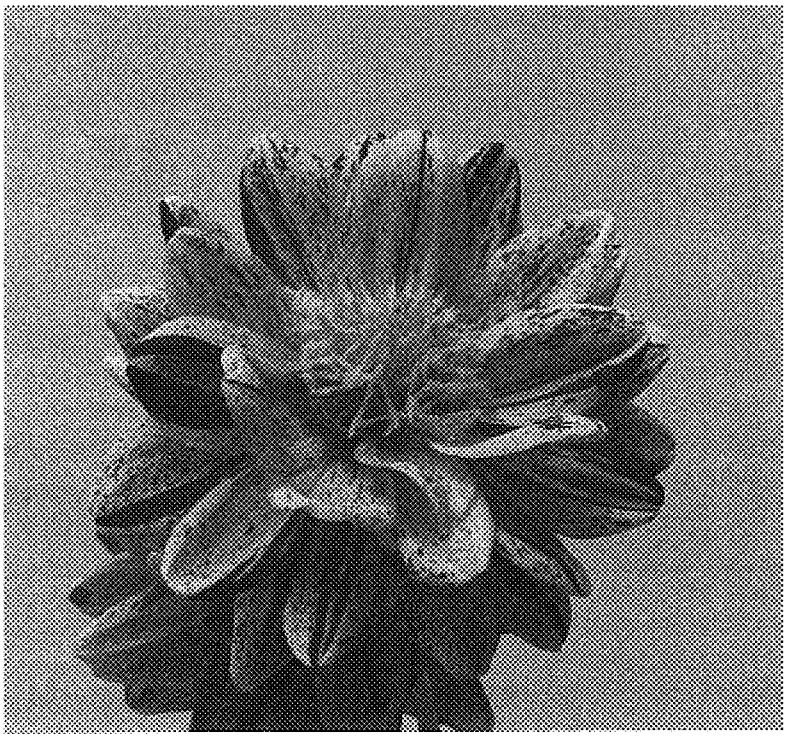

* * * * *